United States Patent
Lahiri et al.

(10) Patent No.: US 10,550,270 B2
(45) Date of Patent: Feb. 4, 2020

(54) COLORLESS COPPER-CONTAINING MATERIAL

(71) Applicant: CORNING INCORPORATED, Corning, NY (US)

(72) Inventors: Joydeep Lahiri, Painted Post, NY (US); Jeffrey Glenn Lynn, Tioga, PA (US); Florence Christine Monique Verrier, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 104 days.

(21) Appl. No.: 15/737,410

(22) PCT Filed: Jun. 22, 2016

(86) PCT No.: PCT/US2016/038648
§ 371 (c)(1),
(2) Date: Dec. 18, 2017

(87) PCT Pub. No.: WO2016/209884
PCT Pub. Date: Dec. 29, 2016

(65) Prior Publication Data
US 2018/0171156 A1    Jun. 21, 2018

Related U.S. Application Data

(60) Provisional application No. 62/185,193, filed on Jun. 26, 2015.

(51) Int. Cl.
| | |
|---|---|
| *C09D 5/14* | (2006.01) |
| *C08K 3/40* | (2006.01) |
| *C08K 5/36* | (2006.01) |
| *C08K 3/015* | (2018.01) |
| *C09D 7/40* | (2018.01) |
| *C08K 3/22* | (2006.01) |

(52) U.S. Cl.
CPC ............... *C09D 5/14* (2013.01); *C08K 3/015* (2018.01); *C08K 3/40* (2013.01); *C08K 5/36* (2013.01); *C09D 7/40* (2018.01); *C08K 2003/2241* (2013.01); *C08K 2003/2248* (2013.01); *C08K 2201/014* (2013.01)

(58) Field of Classification Search
CPC ........ A01N 25/08; A01N 25/34; A01N 59/20; A01N 59/24; C03C 3/064; C03C 4/02; C03C 14/004; C03C 2214/04; C08K 3/40; C08K 3/015; C08K 5/36; C08K 7/20; C08K 2003/2241; C08K 2003/2248; C08K 2201/014; C09D 5/14; C09D 5/1618; C09D 7/40; C09D 7/61
See application file for complete search history.

(56) References Cited

U.S. PATENT DOCUMENTS

| | | | |
|---|---|---|---|
| 5,614,006 A | 3/1997 | Algar | |
| 5,646,198 A * | 7/1997 | Tanaka ................. | C09D 5/1668 106/18.31 |
| 8,889,164 B2 | 11/2014 | Hashimoto et al. | |
| 9,622,483 B2 | 4/2017 | Bookbinder et al. | |
| 2014/0271757 A1 | 9/2014 | Agrawal et al. | |

FOREIGN PATENT DOCUMENTS

| | | |
|---|---|---|
| WO | 2012063679 A1 | 5/2012 |
| WO | 2014091861 A1 | 6/2014 |

OTHER PUBLICATIONS

International Search Report and Written Opinion of the International Searching Authority; PCT/US2016/038648; dated Sep. 5, 2016; 12 Pages; European Patent Office.

* cited by examiner

*Primary Examiner* — Anthony J Green
(74) *Attorney, Agent, or Firm* — John P. Ciccarelli (57) ABSTRACT

Aspects of this disclosure pertain to a colorless material that includes a carrier, copper-containing particles, and either one or both of sodium thiocyanate and titanium dioxide. In one or more embodiments, the material exhibits, in the CIE L*a*b* system, an L* value in the range from about 91 to about 100, and a C* value of less than about 7, wherein C* equals $\sqrt{(a^{*2}+b^{*2})}$. In some embodiments, the material exhibits a greater than 3 log reduction in a concentration of *Staphylococcus aureus*, under the EPA Test Method for Efficacy of Copper Alloy as a Sanitizer testing conditions.

12 Claims, 4 Drawing Sheets

COLORLESS COPPER-CONTAINING MATERIAL

CROSS-REFERENCE TO RELATED APPLICATIONS

This application is a national stage entry of International Patent Application Serial No. PCT/US16/38648 filed on Jun. 22, 2016, which the benefit of priority under 35 U.S.C. § 119 of U.S. Provisional Application Ser. No. 62/185,193 filed on Jun. 26, 2015, the content of which are relied upon and incorporated herein by reference in their entirety.

BACKGROUND

The disclosure relates to copper-containing material that is colorless and maintains antimicrobial activity, and more particularly to paint including copper-containing glass particles or cuprous oxide particles, and either one or more of sodium thiocyanate and titanium dioxide.

Cuprous oxide and metallic copper have been used as an antimicrobial additive in various materials; however, copper is highly colored and may not be used when a white or colorless material is desired. Colorants may be added to adjust the color, but often results in muted colors or a cream or non-white color. Moreover, colorants and other additives may reduce the antimicrobial activity of the material. For example, cuprous thiocyanate is a white pigment that can be employed to adjust the color of the paint, especially when applied to a surface; however, while enabling an off-white color, it does not exhibit the high antimicrobial activity. Accordingly, there is a need for a material that is colorless while maintaining high antimicrobial activity. More specifically, there is a need for a decorative paint that exhibits colorlessness and high antimicrobial activity.

SUMMARY

A first aspect of this disclosure pertains to a colorless material that includes a carrier, copper-containing particles, and either one or both of sodium thiocyanate and titanium dioxide. In one or more embodiments, the material exhibits, in the CIE L*a*b* system, an L* value in the range from about 91 to about 100, and a C* value of less than about 7, wherein C* equals $\sqrt{(a^{*2}+b^{*2})}$. In some embodiments, the material exhibits a greater than 3 log reduction in a concentration of Staphylococcus aureus, under the EPA Test Method for Efficacy of Copper Alloy as a Sanitizer testing conditions.

The copper-containing particles include a copper-containing glass, cuprous oxide or a combination thereof. In some embodiments, the copper-containing particles consist essentially of a copper-containing glass. The amount of copper-containing particles in the material may be about 200 g/gallon of the carrier or less (e.g., in the range from about 100 g/gallon of carrier to about 200 g/gallon of carrier). Where sodium thiocyanate is utilized, it is present in an amount of about 20 g/gallon or less. Where titanium dioxide is utilized, it is present in an amount of about 5 wt % or less.

The carriers used in one or more embodiments may include a polymer, a monomer, a binder or a solvent. In some instances the carrier is a paint.

A second aspect of this disclosure pertains to a paint including a plurality of copper ions. The paint of one or more embodiments exhibits a 99% or greater reduction in a concentration of Staphylococcus aureus, under the EPA Test Method for Efficacy of Copper Alloy as a Sanitizer testing conditions. In some instances, the paint exhibits, in the CIE L*a*b* system, an L* value in the range from about 90 to about 100, and a C* value of less than about 9, wherein C* equals $\sqrt{(a^{*2}+b^{*2})}$.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

DETAILED DESCRIPTION

Reference will now be made in detail to various embodiments. A first aspect of this disclosure pertains to a colorless material that exhibits a white or colorless appearance, and antimicrobial activity that meets the health benefit requirements set forth by the United States Environmental Protection Agency (EPA). Specifically, the material exhibits a kill rate of greater than 99.9% (or a log reduction of 3 or greater) within 2 hours of exposure to Staphylococcus aureus under the EPA Test Method for Efficacy of Copper Alloy as a Sanitizer testing conditions (the "EPA Test").

As used herein the term "antimicrobial," means a material, or a surface of a material that will kill or inhibit the growth of microbes including bacteria, viruses and/or fungi. The term as used herein does not mean the material or the surface of the material will kill or inhibit the growth of all species microbes within such families, but that it will kill or inhibit the growth or one or more species of microbes from such families.

As used herein the term "log reduction" means—log $(C_a/C_0)$, where Ca=the colony form unit (CFU) number of the antimicrobial surface and $C_0$=the colony form unit (CFU) of the control surface that is not an antimicrobial surface. As an example, a 3 log reduction equals about 99.9% of the microbes killed and a Log Reduction of 5=99.999% of microbes killed.

In one or more embodiments, the colorless material includes a carrier, copper-containing particles, and either one or both of sodium thiocyanate and titanium dioxide. In one or more embodiments, the colorlessness of the material can be characterized under the CIE L*a*b* colorimetry system. In one or more embodiments, the material exhibits an L* value in the range from about 88 to about 100 (e.g., from about 90 to about 100, from about 91 to about 100, from about 92 to about 100, from about 93 to about 100, from about 94 to about 100, from about 88 to about 98, from about 88 to about 96, from about 88 to about 95, or from about 88 to about 94). In one or more embodiments, the material exhibits a C* value of less than about 10, wherein C* equals $\sqrt{(a*^2+b*^2)}$. The C* value exhibited by the material of one or more embodiment may be less than about 9, less than about 8, less than about 7, less than about 6, less than about 5 or less than about 4. In some instances, the C* value may even be less than about 3 or 2. The L*, a*, and b* values described herein are measured at normal incidence using a standard illuminant as determined by the CIE, including an A illuminant (representing tungsten-filament lighting), B illuminant (representing daylight simulating illuminants), C illuminant (representing daylight simulating illuminants), D illuminant (representing natural daylight), and F illuminant (representing various types of fluorescent lighting). In some embodiments, the L*, a*, and b* values described herein are measured under CIE D65 of F2 illuminant.

In some embodiments, the material exhibits the L*, a*, and b* values described herein after application of the material on a surface as a layer. In specific embodiments, the resulting layer exhibits the L*, a*, and b* values described herein. In such embodiments, the material may include titanium dioxide and exhibits the L*, a*, and b* values described herein after application of the material to a surface (e.g., about 2 minutes after formation of the layer, 5 minutes after formation of the layer or about 10 minutes or more after formation of the layer). In some embodiments, the layer becomes whiter or more colorless with time. In some instances, the L*, a*, and b* values described herein are exhibited after about 20 minutes, after 30 minutes, after 45 minutes, after 60 minutes, after the formation of the layer. The L*, a*, and b* values are exhibited after drying in air and without any post treatment (e.g., exposure to ultra-violet light etc.).

In one or more embodiments, the material exhibits a whiter or more colorless appearance immediately after combination. For example, in some embodiments, material stored for one week or more (without application to a surface) appeared white and colorless.

In one or more embodiments, the material exhibits a greater than 3 log reduction in a concentration of *Staphylococcus aureus*, under the EPA Test.

In one or more embodiments, the material may exhibit a 2 log reduction or greater (e.g., 4 log reduction or greater, or a 5 log reduction or greater) in a concentration of Murine Norovirus, under modified JIS Z 2801 (2000) testing conditions for evaluating viruses (hereinafter, "Modified JIS Z 2801 for Viruses"). The Modified JIS Z 2801 (2000) Test for Viruses is described in greater detail herein.

In some embodiments, the material may exhibit the log reductions described herein (i.e., under the EPA Test, the Modified JIS Z 2801 Test for Bacteria and/or the Modified JIS Z 2801 Test for Viruses), for a period of one month or greater or for a period of three months or greater. The one month period or three month period may commence at or after the application of the material to a surface as a layer. In such the layer exhibits the log reductions described herein.

The copper-containing particles may include a copper-containing glass, cuprous oxide or a combination thereof. In some instances, the copper-containing particles include only copper-containing glass or only cuprous oxide.

One or more embodiments of the copper-containing glass include a Cu species. In one or more alternative embodiments, the Cu species may include $Cu^{1+}$, $Cu^0$, and/or $Cu^{2+}$. The combined total of the Cu species may be about 10 wt % or more. However, as will be discussed in more detail below, the amount of $Cu^{2+}$ is minimized or is reduced such that the copper-containing glass is substantially free of $Cu^{2+}$. The $Cu^{1+}$ ions may be present on or in the surface and/or the bulk of the copper-containing glass. In some embodiments, the $Cu^{1+}$ ions are present in a glass network and/or a glass matrix of the copper-containing glass. Where the $Cu^{1+}$ ions are present in the glass network, the $Cu^{1+}$ ions are atomically bonded to the atoms in the glass network. Where the $Cu^{1+}$ ions are present in the glass matrix, the $Cu^{1+}$ ions may be present in the form of $Cu^{1+}$ crystals that are dispersed in the glass matrix. In some embodiments the $Cu^{1+}$ crystals include cuprite ($Cu_2O$). In such embodiments, where $Cu^{1+}$ crystals are present, the material may be referred to as a copper-containing glass ceramic, which is intended to refer to a specific type of glass with crystals that may or may not be subjected to a traditional ceramming process by which one or more crystalline phases are introduced and/or generated in the glass. Where the $Cu^{1+}$ ions are present in a non-crystalline form, the material may be referred to as a copper-containing glass. In some embodiments, both $Cu^{1+}$ crystals and $Cu^{1+}$ ions not associated with a crystal are present in the copper-containing glasses described herein.

In one or more embodiments, the copper-containing glass may be formed from a glass composition that can include, in mole percent, $SiO_2$ in the range from about 30 to about 70, $Al_2O_3$ in the range from about 0 to about 20, a copper-containing oxide in the range from about 10 to about 50, CaO in the range from about 0 to about 15, MgO in the range from about 0 to about 15, $P_2O_5$ in the range from about 0 to about 25, $B_2O_3$ in the range from about 0 to about 25, $K_2O$ in the range from about 0 to about 20, ZnO in the range from about 0 to about 5, $Na_2O$ in the range from about 0 to about 20, and/or $Fe_2O_3$ in the range from about 0 to about 5. In such embodiments, the amount of the copper-containing oxide is greater than the amount of $Al_2O_3$. In some embodiments, the glass composition may include a content of $R_2O$, where R may include K, Na, Li, Rb, Cs and combinations thereof.

In the embodiments of the glass compositions described herein, $SiO_2$ serves as the primary glass-forming oxide. The amount of $SiO_2$ present in a glass composition should be enough to provide glasses that exhibit the requisite chemical durability suitable for its use or application (e.g., touch applications, article housing etc.). The upper limit of $SiO_2$ may be selected to control the melting temperature of the glass compositions described herein. For example, excess $SiO_2$ could drive the melting temperature at 200 poise to high temperatures at which defects such as fining bubbles may appear or be generated during processing and in the resulting glass. Furthermore, compared to most oxides, $SiO_2$ decreases the compressive stress created by an ion exchange process of the resulting glass. In other words, glass formed from glass compositions with excess $SiO_2$ may not be ion-exchangeable to the same degree as glass formed from glass compositions without excess $SiO_2$. Additionally or alternatively, $SiO_2$ present in the glass compositions according to one or more embodiments could increase the plastic deformation prior break properties of the resulting glass. An increased $SiO_2$ content in the glass formed from the glass compositions described herein may also increase the indentation fracture threshold of the glass.

In one or more embodiments, the glass composition includes $SiO_2$ in an amount, in mole percent, in the range from about 30 to about 70, from about 30 to about 69, from about 30 to about 68, from about 30 to about 67, from about 30 to about 66, from about 30 to about 65, from about 30 to about 64, from about 30 to about 63, from about 30 to about 62, from about 30 to about 61, from about 30 to about 60, from about 40 to about 70, from about 45 to about 70, from about 46 to about 70, from about 48 to about 70, from about 50 to about 70, from about 41 to about 69, from about 42 to about 68, from about 43 to about 67 from about 44 to about 66 from about 45 to about 65, from about 46 to about 64, from about 47 to about 63, from about 48 to about 62, from about 49 to about 61, from about 50 to about 60 and all ranges and sub-ranges therebetween.

In one or more embodiments, the glass composition includes $Al_2O_3$ an amount, in mole percent, in the range from about 0 to about 20, from about 0 to about 19, from about 0 to about 18, from about 0 to about 17, from about 0 to about 16, from about 0 to about 15, from about 0 to about 14, from about 0 to about 13, from about 0 to about 12, from about 0 to about 11 from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition is substantially free of $Al_2O_3$. As used herein, the phrase "substantially free" with respect to the components of the glass composition and/or resulting glass means that the component is not actively or intentionally added to the glass compositions during initial batching or subsequent post processing (e.g., ion exchange process), but may be present as an impurity. For example, a glass composition, a glass may be describe as being substantially free of a component, when the component is present in an amount of less than about 0.01 mol %.

The amount of $Al_2O_3$ may be adjusted to serve as a glass-forming oxide and/or to control the viscosity of molten glass compositions. Without being bound by theory, it is believed that when the concentration of alkali oxide ($R_2O$) in a glass composition is equal to or greater than the concentration of $Al_2O_3$, the aluminum ions are found in tetrahedral coordination with the alkali ions acting as charge-balancers. This tetrahedral coordination greatly enhances various post-processing (e.g., ion exchange process) of glasses formed from such glass compositions. Divalent cation oxides (RO) can also charge balance tetrahedral aluminum to various extents. While elements such as calcium, zinc, strontium, and barium behave equivalently to two alkali ions, the high field strength of magnesium ions causes them to not fully charge balance aluminum in tetrahedral coordination, resulting in the formation of five- and six-fold coordinated aluminum. Generally, $Al_2O_3$ can play an important role in ion-exchangeable glass compositions and strengthened glasses since it enables a strong network backbone (i.e., high strain point) while allowing for the relatively fast diffusivity of alkali ions. However, when the concentration of $Al_2O_3$ is too high, the glass composition may exhibit lower liquidus viscosity and, thus, $Al_2O_3$ concentration may be controlled within a reasonable range. Moreover, as will be discussed in more detail below, excess $Al_2O_3$ has been found to promote the formation of $Cu^{2+}$ ions, instead of the desired $Cu^{1+}$ ions.

In one or more embodiments, the glass composition includes a copper-containing oxide in an amount, in mole percent, in the range from about 10 to about 50, from about 10 to about 49, from about 10 to about 48, from about 10 to about 47, from about 10 to about 46, from about 10 to about 45, from about 10 to about 44, from about 10 to about 43, from about 10 to about 42, from about 10 to about 41, from about 10 to about 40, from about 10 to about 39, from about 10 to about 38, from about 10 to about 37, from about 10 to about 36, from about 10 to about 35, from about 10 to about 34, from about 10 to about 33, from about 10 to about 32, from about 10 to about 31, from about 10 to about 30, from about 10 to about 29, from about 10 to about 28, from about 10 to about 27, from about 10 to about 26, from about 10 to about 25, from about 10 to about 24, from about 10 to about 23, from about 10 to about 22, from about 10 to about 21, from about 10 to about 20, from about 11 to about 50, from about 12 to about 50, from about 13 to about 50, from about 14 to about 50, from about 15 to about 50, from about 16 to about 50, from about 17 to about 50, from about 18 to about 50, from about 19 to about 50, from about 20 to about 50, from about 10 to about 30, from about 11 to about 29, from about 12 to about 28, from about 13 to about 27, from about 14 to about 26, from about 15 to about 25, from about 16 to about 24, from about 17 to about 23, from about 18 to about 22, from about 19 to about 21 and all ranges and sub-ranges therebetween. In one or more specific embodiments, the copper-containing oxide may be present in the glass composition in an amount of about 20 mole percent, about 25 mole percent, about 30 mole percent or about 35 mole percent. The copper-containing oxide may include CuO, $Cu_2O$ and/or combinations thereof.

The copper-containing oxides in the glass composition form the $Cu^{1+}$ ions present in the resulting glass. Copper may be present in the glass composition and/or the glasses including the glass composition in various forms including $Cu^0$, $Cu^{1+}$, and $Cu^{2+}$. Copper in the $Cu^0$ or $Cu^{1+}$ forms provide antimicrobial activity. However forming and maintaining these states of antimicrobial copper are difficult and often, in known glass compositions, $Cu^{2+}$ ions are formed instead of the desired $Cu^0$ or $Cu^{1+}$ ions.

In one or more embodiments, the amount of copper-containing oxide is greater than the amount of $Al_2O_3$ in the glass composition. Without being bound by theory it is believed that an about equal amount of copper-containing oxides and $Al_2O_3$ in the glass composition results in the formation of tenorite (CuO) instead of cuprite ($Cu_2O$). The presence of tenorite decreases the amount of $Cu^{1+}$ in favor of $Cu^{2+}$ and thus leads to reduced antimicrobial activity. Moreover, when the amount of copper-containing oxides is about equal to the amount of $Al_2O_3$, aluminum prefers to be in a four-fold coordination and the copper in the glass composition and resulting glass remains in the $Cu^{2+}$ form so that the charge remains balanced. Where the amount of copper-containing oxide exceeds the amount of $Al_2O_3$, then it is believed that at least a portion of the copper is free to remain in the $Cu^{1+}$ state, instead of the $Cu^{2+}$ state, and thus the presence of $Cu^{1+}$ ions increases.

The glass composition of one or more embodiments includes $P_2O_5$ in an amount, in mole percent, in the range from about 0 to about 25, from about 0 to about 22, from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition includes about 10 mole percent or about 5 mole percent $P_2O_5$ or, alternatively, may be substantially free of $P_2O_5$.

In one or more embodiments, $P_2O_5$ forms at least part of a less durable phase or a degradable phase in the glass. The relationship between the degradable phase(s) of the glass and antimicrobial activity is discussed in greater detail herein. In one or more embodiments, the amount of $P_2O_5$ may be adjusted to control crystallization of the glass composition and/or glass during forming. For example, when the amount of $P_2O_5$ is limited to about 5 mol % or less or even 10 mol % or less, crystallization may be minimized or controlled to be uniform. However, in some embodiments, the amount or uniformity of crystallization of the glass composition and/or glass may not be of concern and thus, the amount of $P_2O_5$ utilized in the glass composition may be greater than 10 mol %.

In one or more embodiments, the amount of $P_2O_5$ in the glass composition may be adjusted based on the desired damage resistance of the glass, despite the tendency for $P_2O_5$ to form a less durable phase or a degradable phase in the glass. Without being bound by theory, $P_2O_5$ can decrease the melting viscosity relative to $SiO_2$. In some instances, $P_2O_5$ is believed to help to suppress zircon breakdown viscosity (i.e., the viscosity at which zircon breaks down to form $ZrO_2$) and may be more effective in this regard than $SiO_2$. When glass is to be chemically strengthened via an ion exchange process, $P_2O_5$ can improve the diffusivity and decrease ion exchange times, when compared to other components that are sometimes characterized as network formers (e.g., $SiO_2$ and/or $B_2O_3$).

The glass composition of one or more embodiments includes $B_2O_3$ in an amount, in mole percent, in the range from about 0 to about 25, from about 0 to about 22, from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition includes a non-zero amount of $B_2O_3$, which may be, for example, about 10 mole percent or about 5 mole percent. The glass composition of some embodiments may be substantially free of $B_2O_3$.

In one or more embodiments, $B_2O_3$ forms a less durable phase or a degradable phase in the glass formed form the glass composition. The relationship between the degradable phase(s) of the glass and antimicrobial activity is discussed in greater detail herein. Without being bound by theory, it is believed the inclusion of $B_2O_3$ in glass compositions imparts damage resistance in glasses incorporating such glass compositions, despite the tendency for $B_2O_3$ to form a less durable phase or a degradable phase in the glass. The glass composition of one or more embodiments includes one or more alkali oxides ($R_2O$) (e.g., $Li_2O$, $Na_2O$, $K_2O$, $Rb_2O$ and/or $Cs_2O$). In some embodiments, the alkali oxides modify the melting temperature and/or liquidus temperatures of such glass compositions. In one or more embodiments, the amount of alkali oxides may be adjusted to provide a glass composition exhibiting a low melting temperature and/or a low liquidus temperature. Without being bound by theory, the addition of alkali oxide(s) may increase the coefficient of thermal expansion (CTE) and/or lower the chemical durability of the copper-containing glasses that include such glass compositions. In some cases these attributes may be altered dramatically by the addition of alkali oxide(s).

In some embodiments, the copper-containing glasses disclosed herein may be chemically strengthened via an ion exchange process in which the presence of a small amount of alkali oxide (such as $Li_2O$ and $Na_2O$) is required to facilitate ion exchange with larger alkali ions (e.g., $K^+$), for example exchanging smaller alkali ions from an copper-containing glass with larger alkali ions from a molten salt bath containing such larger alkali ions. Three types of ion exchange can generally be carried out. One such ion exchange includes a $Na^+$-for-$Li^+$ exchange, which results in a deep depth of layer but low compressive stress. Another such ion exchange includes a $K^+$-for-$Li^+$ exchange, which results in a small depth of layer but a relatively large compressive stress. A third such ion exchange includes a $K^+$-for-$Na^+$ exchange, which results in intermediate depth of layer and compressive stress. A sufficiently high concentration of the small alkali oxide in glass compositions may be necessary to produce a large compressive stress in the copper-containing glass including such glass compositions, since compressive stress is proportional to the number of alkali ions that are exchanged out of the copper-containing glass.

In one or more embodiments, the glass composition includes $K_2O$ in an amount in the range from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition includes a non-zero amount of $K_2O$ or, alternatively, the glass composition may be substantially free, as defined herein, of $K_2O$. In addition to facilitating ion exchange, where applicable, in one or more embodiments, $K_2O$ can also form a less durable phase or a degradable phase in the glass formed form the glass composition. The relationship between the degradable phase(s) of the glass and antimicrobial activity is discussed in greater detail herein.

In one or more embodiments, the glass composition includes $Na_2O$ in an amount in the range from about 0 to about 20, from about 0 to about 18, from about 0 to about 16, from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition includes a non-zero amount of $Na_2O$ or, alternatively, the glass composition may be substantially free, as defined herein, of $Na_2O$.

In one or more embodiments, the glass composition may include one or more divalent cation oxides, such as alkaline earth oxides and/or ZnO. Such divalent cation oxides may be included to improve the melting behavior of the glass compositions. With respect to ion exchange performance, the presence of divalent cations can act to decrease alkali mobility and thus, when larger divalent cation oxides are utilized, there may be a negative effect on ion exchange performance. Furthermore, smaller divalent cation oxides generally help the compressive stress developed in an ion-exchanged glass more than the larger divalent cation oxides. Hence, divalent cation oxides such as MgO and ZnO can offer advantages with respect to improved stress relaxation, while minimizing the adverse effects on alkali diffusivity.

In one or more embodiments, the glass composition includes CaO in an amount, in mole percent, in the range from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition is substantially free of CaO.

In one or more embodiments, the glass composition includes MgO in an amount, in mole percent, in the range from about 0 to about 15, from about 0 to about 14, from about 0 to about 13, from about 0 to about 12, from about 0 to about 11, from about 0 to about 10, from about 0 to about 9, from about 0 to about 8, from about 0 to about 7, from about 0 to about 6, from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition is substantially free of MgO.

The glass composition of one or more embodiments may include ZnO in an amount, in mole percent, in the range from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition is substantially free of ZnO.

The glass composition of one or more embodiments may include $Fe_2O_3$, in mole percent, in the range from about 0 to about 5, from about 0 to about 4, from about 0 to about 3, from about 0 to about 2, from about 0 to about 1, from about 0.1 to about 1, from about 0.2 to about 1, from about 0.3 to about 1 from about 0.4 to about 1 from about 0.5 to about 1, from about 0 to about 0.5, from about 0 to about 0.4, from about 0 to about 0.3 from about 0 to about 0.2, from about 0 to about 0.1 and all ranges and sub-ranges therebetween. In some embodiments, the glass composition is substantially free of $Fe_2O_3$.

In one or more embodiments, the glass composition may include one or more colorants. Examples of such colorants include NiO, $TiO_2$, $Fe_2O_3$, $Cr_2O_3$, $Co_3O_4$ and other known colorants. In some embodiments, the one or more colorants may be present in an amount in the range up to about 10 mol %. In some instances, the one or more colorants may be present in an amount in the range from about 0.01 mol % to about 10 mol %, from about 1 mol % to about 10 mol %, from about 2 mol % to about 10 mol %, from about 5 mol % to about 10 mol %, from about 0.01 mol % to about 8 mol %, or from about 0.01 mol % to about 5 mol %.

In one or more embodiments, the glass composition may include one or more nucleating agents. Exemplary nucleating agents include $TiO_2$, $ZrO_2$ and other known nucleating agents in the art. The glass composition can include one or more different nucleating agents. The nucleating agent content of the glass composition may be in the range from about 0.01 mol % to about 1 mol %. In some instances, the nucleating agent content may be in the range from about 0.01 mol % to about 0.9 mol %, from about 0.01 mol % to about 0.8 mol %, from about 0.01 mol % to about 0.7 mol %, from about 0.01 mol % to about 0.6 mol %, from about 0.01 mol % to about 0.5 mol %, from about 0.05 mol % to about 1 mol %, from about 0.1 mol % to about 1 mol %, from about 0.2 mol % to about 1 mol %, from about 0.3 mol % to about 1 mol %, or from about 0.4 mol % to about 1 mol %, and all ranges and sub-ranges therebetween.

The copper-containing glasses formed from the glass compositions may include a plurality of $Cu^{1+}$ ions. In some embodiments, such $Cu^{1+}$ ions form part of the glass network and may be characterized as a glass modifier. Without being bound by theory, where $Cu^{1+}$ ions are part of the glass network, it is believed that during typical glass formation processes, the cooling step of the molten glass occurs too rapidly to allow crystallization of the copper-containing oxide (e.g., CuO and/or $Cu_2O$). Thus the $Cu^{1+}$ remains in an amorphous state and becomes part of the glass network. In some cases, the total amount of $Cu^{1+}$ ions, whether they are in a crystalline phase or in the glass matrix, may be even higher, such as up to 40 mol %, up to 50 mol %, or up to 60 mol %.

In one or more embodiments, the copper-containing glasses formed form the glass compositions disclosed herein include $Cu^{1+}$ ions that are dispersed in the glass matrix as $Cu^{1+}$ crystals. In one or more embodiments, the $Cu^{1+}$ crystals may be present in the form of cuprite. The cuprite present in the copper-containing glass may form a phase that is distinct from the glass matrix or glass phase. In other embodiments, the cuprite may form part of or may be associated with one or more glasses phases (e.g., the durable phase described herein). The $Cu^{1+}$ crystals may have an average major dimension of about 5 micrometers (μm) or less, 4 micrometers (μm) or less, 3 micrometers (μm) or less, 2 micrometers (μm) or less, about 1.9 micrometers (μm) or less, about 1.8 micrometers (μm) or less, about 1.7 micrometers (μm) or less, about 1.6 micrometers (μm) or less, about 1.5 micrometers (μm) or less, about 1.4 micrometers (μm) or less, about 1.3 micrometers (μm) or less, about 1.2 micrometers (μm) or less, about 1.1 micrometers or less, 1 micrometers or less, about 0.9 micrometers (μm) or less, about 0.8 micrometers (μm) or less, about 0.7 micrometers (μm) or less, about 0.6 micrometers (μm) or less, about 0.5 micrometers (μm) or less, about 0.4 micrometers (μm) or less, about 0.3 micrometers (μm) or less, about 0.2 micrometers (μm) or less, about 0.1 micrometers (μm) or less, about 0.05 micrometers (μm) or less, and all ranges and sub-ranges therebetween. As used herein and with respect to the phrase "average major dimension", the word "average" refers to a mean value and the word "major dimension" is the greatest dimension of the particle as measured by SEM. In some embodiments, the cuprite phase may be present in the copper-containing glass in an amount of at least about 10 wt %, at least about 15 wt %, at least about 20 wt %, at least about 25 wt % and all ranges and subranges therebetween of the copper-containing glass.

In some embodiments, the copper-containing glass may include about 70 wt % $Cu^{1+}$ or more and about 30 wt % of $Cu^{2+}$ or less. The $Cu^{2+}$ ions may be present in tenorite form and/or even in the glass (i.e., not as a crystalline phase).

In some embodiments, the total amount of Cu by wt % in the copper-containing glass may be in the range from about 10 to about 30, from about 15 to about 25, from about 11 to about 30, from about 12 to about 30, from about 13 to about 30, from about 14 to about 30, from about 15 to about 30, from about 16 to about 30, from about 17 to about 30, from about 18 to about 30, from about 19 to about 30, from about 20 to about 30, from about 10 to about 29, from about 10 to about 28, from about 10 to about 27, from about 10 to about 26, from about 10 to about 25, from about 10 to about 24, from about 10 to about 23, from about 10 to about 22, from about 10 to about 21, from about 10 to about 20, from about 16 to about 24, from about 17 to about 23, from about 18 to about 22, from about 19 to about 21 and all ranges and sub-ranges therebetween. In one or more embodiments, the ratio of $Cu^{1+}$ ions to the total amount Cu in the copper-containing glass is about 0.5 or greater, 0.55 or greater, 0.6 or greater, 0.65 or greater, 0.7 or greater, 0.75 or greater, 0.8 or greater, 0.85 or greater, 0.9 or greater or even 1 or greater, and all ranges and sub-ranges therebetween. The amount of Cu and the ratio of $Cu^{1+}$ ions to total Cu may be determined by inductively coupled plasma (ICP) techniques known in the art.

In some embodiments, the copper-containing glass may exhibit a greater amount of $Cu^{1+}$ and/or Cu0 than $Cu^{2+}$. For example, based on the total amount of $Cu^{1+}$, $Cu^{2+}$ and Cu0 in the glasses, the percentage of $Cu^{1+}$ and $Cu^0$, combined, may be in the range from about 50% to about 99.9%, from about 50% to about 99%, from about 50% to about 95%, from about 50% to about 90%, from about 55% to about 99.9%, from about 60% to about 99.9%, from about 65% to about 99.9%, from about 70% to about 99.9%, from about 75% to about 99.9%, from about 80% to about 99.9%, from about 85% to about 99.9%, from about 90% to about 99.9%, from about 95% to about 99.9%, and all ranges and sub-ranges therebetween. The relative amounts of $Cu^{1+}$, $Cu^{2+}$ and $Cu^0$ may be determined using x-ray photoluminescence spectroscopy (XPS) techniques known in the art. The copper-containing glass comprises at least a first phase and second phase. In one or more embodiments, the copper-containing glass may include two or more phases wherein the phases differ based on the ability of the atomic bonds in the given phase to withstand interaction with a leachate. Specifically, the copper-containing glass of one or more embodiments may include a first phase that may be described as a degradable phase and a second phase that may be described as a durable phase. The phrases "first phase" and "degradable phase" may be used interchangeably. The phrases "second phase" and "durable phase" may be used interchangeably. As used herein, the term "durable" refers to the tendency of the atomic bonds of the durable phase to remain intact during and after interaction with a leachate. As used herein, the term "degradable" refers to the tendency of the atomic bonds of the degradable phase to break during and after interaction with one or more leachates. In one or more embodiments, the durable phase includes $SiO_2$ and the degradable phase includes at least one of $B_2O_3$, $P_2O_5$ and $R_2O$ (where R can include any one or more of K, Na, Li, Rb, and Cs). Without being bound by theory, it is believed that the components of the degradable phase (i.e., $B_2O_3$, $P_2O_5$ and/or $R_2O$) more readily interact with a leachate and the bonds between these components to one another and to other components in the copper-containing glass more readily break during and after the interaction with the leachate. Leachates may include water, acids or other similar materials. In one or more embodiments, the degradable phase withstands degradation for 1 week or longer, 1 month or longer, 3 months or longer, or even 6 months or longer. In some embodiments, longevity may be characterized as maintaining antimicrobial efficacy over a specific period of time.

In one or more embodiments, the durable phase is present in an amount by weight that is greater than the amount of the degradable phase. In some instances, the degradable phase forms islands and the durable phase forms the sea surrounding the islands (i.e., the durable phase). In one or more embodiments, either one or both of the durable phase and the degradable phase may include cuprite. The cuprite in such embodiments may be dispersed in the respective phase or in both phases.

In some embodiments, phase separation occurs without any additional heat treatment of the copper-containing glass. In some embodiments, phase separation may occur during melting and may be present when the glass composition is melted at temperatures up to and including about 1600° C. or 1650° C. When the glass is cooled, the phase separation is maintained.

The copper-containing glass may be provided as a sheet or may have another shape such as particulate (which may be hollow or solid), fibrous, and the like. In one or more embodiments, the copper-containing glass includes a surface and a surface portion extending from the surface into the copper-containing glass at a depth of about 5 nanometers (nm) or less. The surface portion may include a plurality of copper ions wherein at least 75% of the plurality of copper ions includes $Cu^{1+}$-ions. For example, in some instances, at least about 80%, at least about 85%, at least about 90%, at least about 95%, at least about 98%, at least about 99% or at least about 99.9% of the plurality of copper ions in the surface portion includes $Cu^{1+}$ ions. In some embodiments, 25% or less (e.g., 20% or less, 15% or less, 12% or less, 10% or less or 8% or less) of the plurality of copper ions in the surface portion include $Cu^{2+}$ ions. For example, in some instances, 20% or less, 15% or less, 10% or less, 5% or less, 2% or less, 1% or less, 0.5% or less or 0.01% or less of the plurality of copper ions in the surface portion include $Cu^{2+}$ ions. In some embodiments, the surface concentration of $Cu^{1+}$ ions in the copper-containing glass is controlled. In some instances, a $Cu^{1+}$ ion concentration of about 4 ppm or greater can be provided on the surface of the copper-containing glass.

The copper-containing glass of one or more embodiments may a 2 log reduction or greater (e.g., 2.5, 3, 3.5, 4, 4.5, 5, 5.5, 6, 6.5 and all ranges and sub-ranges therebetween) in a concentration of at least one of *Staphylococcus aureus, Enterobacter aerogenes, Pseudomomas aeruginosa*, Methicillin Resistant *Staphylococcus aureus*, and *E. coli*, under the EPA Test. In some instances, the copper-containing glass exhibits at least a 4 log reduction, a 5 log reduction or even a 6 log reduction in the concentration of at least one of *Staphylococcus aureus, Enterobacter aerogenes, Pseudomomas aeruginosa* bacteria, Methicillin Resistant *Staphylococcus aureus*, and *E. coli* under the EPA Test.

The glasses described herein according to one or more embodiments may exhibit a 4 log reduction or greater (e.g., 5 log reduction or greater) in a concentration of at least one of *Staphylococcus aureus, Enterobacter aerogenes, Pseudomomas aeruginosa* bacteria, Methicillin Resistant *Staphylococcus aureus*, and *E. coli*, under JIS Z 2801 (2000) testing conditions. One or more embodiments of the glasses described herein also exhibit a 4 log reduction or greater (e.g., 5 log reduction or greater) in a concentration of at least one of *Staphylococcus aureus, Enterobacter aerogenes, Pseudomomas aeruginosa* Methicillin Resistant *Staphylococcus aureus*, and *E. coli*, under the Modified JIS Z 2801 Test for Bacterial. As used herein, Modified JIS Z 2801 Test for Bacteria includes evaluating the bacteria under the standard JIS Z 2801 (2000) test with modified conditions comprising heating the glass or article to a temperature of about 23 degrees Celsius to about 37 degrees Celsius at a humidity of about 38 percent to about 42 percent for about 6 hours.

In one or more embodiments described herein, the copper-containing glasses exhibit a 2 log reduction or greater, a 3 log reduction or greater, a 4 log reduction or greater, or a 5 log reduction or greater in Murine Norovirus under a Modified JIS Z 2801 for Viruses test. The Modified JIS Z 2801 (2000) Test for Viruses includes the following procedure. For each material (e.g., the articles or glass of one or more embodiments, control materials, and any comparative glasses or articles) to be tested, three samples of the material (contained in individual sterile petri dishes) are each inoculated with a 20 µL aliquot of a test virus (where antimicrobial activity is measured) or a test medium including an organic soil load of 5% fetal bovine serum with or without the test virus (where cytotoxicity is measured). The inoculum is then covered with a film and the film is pressed down so the test virus and/or or test medium spreads over the film, but does not spread past the edge of the film. The exposure time begins when each sample was inoculated. The inoculated samples are transferred to a control chamber set to room temperature (about 20° C.) in a relative humidity of 42% for 2 hours. Exposure time with respect to control samples are discussed below. Following the 2-hour exposure time, the film is lifted off using sterile forceps and a 2.00 mL aliquot of the text virus and/or test medium is pipetted individually onto each sample of material and the underside of the film (or the side of the film exposed to the sample) used to cover each sample. The surface of each sample is individually scrapped with a sterile plastic cell scraper to collect the test virus or test medium. The test virus and/or test medium is collected (at $10^{-2}$ dilution), mixed using a vortex type mixer and serial 10-fold dilutions are prepared. The dilutions are then assayed for antimicrobial activity and/or cytotoxicity.

To prepare a control sample for testing antimicrobial activity (which are also referred to as "zero-time virus controls") for the Modified JIS Z 2801 Test for Viruses, three control samples (contained in individual sterile petri dishes) are each inoculated with a 20 µL aliquot of the test virus. Immediately following inoculation, a 2.00 mL aliquot of test virus is pipetted onto each control sample. The surface of each sample was individually scrapped with a sterile plastic cell scraper to collect test virus. The test virus is collected (at $10^{-2}$ dilution), mixed using a vortex type mixer, and serial 10-fold dilutions were prepared. The dilutions are assayed for antimicrobial activity.

To prepare controls samples for cytotoxicity (which are also referred to as "2 hour control virus") for the Modified JIS Z 2801 Test for Viruses, one control sample (contained in an individual sterile petri dish) is inoculated with a 20 µL aliquot of a test medium containing an organic soil load (5% fetal bovine serum), without the test virus. The inoculum is covered with a film and the film is pressed so the test medium spreads over the film but does not spread past the edge of the film. The exposure time begins when each control sample is inoculated. The control sample is transferred to a controlled chamber set to room temperature (20° C.) in a relative humidity of 42% for a duration of 2 hours exposure time. Following this exposure time, the film is lifted off using sterile forceps and a 2.00 mL aliquot of the test medium is pipetted individually onto each control sample and the underside of the film (the side exposed to the sample). The surface of each sample is individually scrapped with a sterile plastic cell scraper to collect the test medium. The test medium is collected (at $10^{-2}$ dilution), mixed using a vortex type mixer, and serial 10-fold dilutions were prepared. The dilutions were assayed for cytotoxicity.

The copper-containing glass of one or more embodiments may exhibit the log reduction described herein for long periods of time. In other words, the copper-containing glass may exhibit extended or prolonged antimicrobial efficacy. For example, in some embodiments, the copper-containing glass may exhibit the log reductions described herein under the EPA Test, the JIS Z 2801 (2000) testing conditions, the Modified JIS Z 2801 Test for Bacteria and/or the Modified JIS Z 2801 Test for Viruses for up to 1 month, up to 3 months, up to 6 months or up to 12 months after the copper-containing glass is formed or after the copper-containing glass is combined with a carrier (e.g., polymers, monomers, binders, solvents and the like). These time periods may start at or after the copper-containing glass is formed or combined with a carrier.

One or more embodiments, the copper-containing glass may exhibit a preservative function, when combined with carriers described herein. In such embodiments, the copper-containing glass may kill or eliminate, or reduce the growth of various foulants in the carrier. Foulants include fungi, bacteria, viruses and combinations thereof.

In one or more embodiments, the copper-containing glasses and/or materials described herein leach the copper ions when exposed or in contact with a leachate. In one or more embodiments, the copper-containing glass leaches only copper ions when exposed to leachates including water.

In one or more embodiments, the copper-containing glass and/or articles described herein may have a tunable antimicrobial activity release. The antimicrobial activity of the glass and/or materials may be caused by contact between the copper-containing glass and a leachate, such as water, where the leachate causes $Cu^{1+}$ ions to be released from the copper-containing glass. This action may be described as water solubility and the water solubility can be tuned to control the release of the $Cu^{1+}$ ions.

In some embodiments, where the $Cu^{1+}$ ions are disposed in the glass network and/or form atomic bonds with the atoms in the glass network, water or humidity breaks those bonds and the $Cu^{1+}$ ions available for release and may be exposed on the glass or glass ceramic surface.

In one or more embodiments, the copper-containing glass may be formed using formed in low cost melting tanks that are typically used for melting glass compositions such as soda lime silicate. The copper-containing glass may be formed into a sheet using forming processes known in the art. For instance, example forming methods include float glass processes and down-draw processes such as fusion draw and slot draw.

After formation, the copper-containing particles may be formed into sheets and may be shaped, polished or otherwise processed for a desired end use. In some instances, the copper-containing glass may be ground to a powder or particulate form. In other embodiments, the particulate copper-containing glass may be combined with other materials or carriers into articles for various end uses. The combination of the copper-containing glass and such other materials or carriers may be suitable for injection molding, extrusion or coatings or may be drawn into fibers.

In one or more embodiments, the copper-containing particles may include cuprous oxide. The amount of cuprous oxide in the particles may be up to 100%. In other words, the cuprous oxide particles may exclude glass or a glass network.

In one or more embodiments, the copper-containing particles may have a diameter in the range from about 0.1 micrometers (μm) to about 10 micrometers (μm), from about 0.1 micrometers (μm) to about 9 micrometers (μm), from about 0.1 micrometers (μm) to about 8 micrometers (μm), from about 0.1 micrometers (μm) to about 7 micrometers (μm), from about 0.1 micrometers (μm) to about 6 micrometers (μm), from about 0.5 micrometers (μm) to about 10 micrometers (μm), from about 0.75 micrometers (μm) to about 10 micrometers (μm), from about 1 micrometers (μm) to about 10 micrometers (μm), from about 2 micrometers (μm) to about 10 micrometers (μm), from about 3 micrometers (μm) to about 10 micrometers (μm) from about 3 micrometers (μm) to about 6 micrometers (μm), from about 3.5 micrometers (μm) to about 5.5 micrometers (μm), from about 4 micrometers (μm), to about 5 micrometers (μm), and all ranges and sub-ranges therebetween. As used herein, the term "diameter" refers to the longest dimension of the particle. The particulate copper-containing glass may be substantially spherical or may have an irregular shape. The particles may be provided in a solvent and thereafter dispersed in a carrier as otherwise described herein.

In one or more embodiments, the copper-containing particles are present in an amount of about 200 g/gallon of the carrier or less. In some instances, the copper-containing particles are present in an amount in the range from about 10 g/gallon to about 200 g/gallon, from about 15 g/gallon to about 200 g/gallon, from about 20 g/gallon to about 200 g/gallon, from about 25 g/gallon to about 200 g/gallon, from about 30 g/gallon to about 200 g/gallon, from about 35 g/gallon to about 200 g/gallon, from about 40 g/gallon to about 200 g/gallon, from about 45 g/gallon to about 200 g/gallon, from about 50 g/gallon to about 200 g/gallon, from about 5 g/gallon to about 190 g/gallon, from about 5 g/gallon to about 180 g/gallon, from about 5 g/gallon to about 170 g/gallon, from about 5 g/gallon to about 160 g/gallon, from about 5 g/gallon to about 150 g/gallon, from about 5 g/gallon to about 140 g/gallon, from about 5 g/gallon to about 130 g/gallon, from about 5 g/gallon to about 120 g/gallon, from about 5 g/gallon to about 110 g/gallon, from about 5 g/gallon to about 100 g/gallon, from about 5 g/gallon to about 90 g/gallon, from about 5 g/gallon to about 80 g/gallon, from about 5 g/gallon to about 70 g/gallon, from about 5 g/gallon to about 60 g/gallon, or from about 5 g/gallon to about 50 g/gallon (all with reference to gallon of the carrier). In some embodiments, the copper containing particles are present in an amount in the range from about 50 g/gallon to about 150 g/gallon of carrier or from about 100 g/gallon to about 200 g/gallon of carrier.

In one or more embodiments, the carrier may include polymers, monomers, binders, solvents, or a combination thereof as described herein. In a specific embodiment, the carrier is a paint that is used for application to surfaces (which may include interior or exterior surfaces).

The polymer used in the embodiments described herein can include a thermoplastic polymer, a polyolefin, a cured polymer, an ultraviolet- or UV-cured polymer, a polymer emulsion, a solvent-based polymer, and combinations thereof. Examples of suitable polymers include, without limitation: thermoplastics including polystyrene (PS), high impact PS, polycarbonate (PC), nylon (sometimes referred to as polyamide (PA)), poly(acrylonitrile-butadiene-styrene) (ABS), PC-ABS blends, polybutyleneterephthlate (PBT) and PBT co-polymers, polyethyleneterephthalate (PET) and PET co-polymers, polyolefins (PO) including polyethylenes (PE), polypropylenes (PP), cyclicpolyolefins (cyclic-PO), modified polyphenylene oxide (mPPO), polyvinylchloride (PVC), acrylic polymers including polymethyl methacrylate (PMMA), thermoplastic elastomers (TPE), thermoplastic urethanes (TPU), polyetherimide (PEI) and blends of these polymers with each other. Suitable injection moldable thermosetting polymers include epoxy, acrylic, styrenic, phenolic, melamine, urethanes, polyesters and silicone resins. In other embodiments, the polymers may be dissolved in a solvent or dispersed as a separate phase in a solvent and form a polymer emulsion, such as a latex (which is a water emulsion of a synthetic or natural rubber, or plastic obtained by polymerization and used especially in coatings (as paint) and adhesives. Polymers may include fluorinated silanes or other low friction or anti-frictive materials. The polymers can contain impact modifiers, flame retardants, UV inhibitors, antistatic agents, mold release agents, fillers including glass, metal or carbon fibers or particles (including spheres), talc, clay or mica and colorants. Specific examples of monomers include catalyst curable monomers, thermally-curable monomers, radiation-curable monomers and combinations thereof.

In one or more embodiments, the material includes sodium thiocyanate, which may be present in the material an amount of about 100 g/gallon of carrier or less. In some embodiments, sodium thiocyanate is present in the material in an amount in the range from about 10 g/gallon to about 100 g/gallon of carrier. For example, the sodium thiocyanate may be present in an amount in the range from about 10 g/gallon to about 80 g/gallon, from about 10 g/gallon to about 70 g/gallon, from about 10 g/gallon to about 60 g/gallon, from about 10 g/gallon to about 50 g/gallon, from about 10 g/gallon to about 40 g/gallon, from about 15 g/gallon to about 100 g/gallon, from about 20 g/gallon to about 100 g/gallon, from about 25 g/gallon to about 100 g/gallon, from about 30 g/gallon to about 100 g/gallon, from about 40 g/gallon to about 100 g/gallon, from about 50 g/gallon to about 100 g/gallon or from about 10 g/gallon to about 20 g/gallon. In some instances, the material may be substantially free of sodium thiocyanate and may include only titanium dioxide, or may include a combination of sodium thiocyanate and titanium dioxide.

In one or more embodiments, the material includes titanium dioxide ($TiO_2$). Titanium dioxide may be present in an amount of about 5 wt % or less. For example, in some instances, titanium dioxide may be present in the material in an amount in the range from about 0.1 wt % to about 5 wt %, from about 0.1 wt % to about 4.5 wt %, from about 0.1 wt % to about 4 wt %, from about 0.1 wt % to about 3.5 wt %, from about 0.1 wt % to about 3 wt %, from about 0.1 wt % to about 2.5 wt %, from about 0.1 wt % to about 2 wt %, from about 0.1 wt % to about 1.5 wt %, from about 0.1 wt % to about 1 wt %, from about 0.5 wt % to about 5 wt %, from about 1 wt % to about 5 wt %, from about 1.5 wt % to about 5 wt %, from about 2 wt % to about 5 wt %, or from about 0.5 wt % to about 1.5 wt %, of the material. In some instances, the material may be substantially free of titanium dioxide and may include only sodium thiocyanate, or may include a combination of sodium thiocyanate and titanium dioxide.

To improve processability, mechanical properties and interactions between the carrier and the copper-glass particles described herein (including any fillers and/or additives that may be used), processing agents/aids may be included in the articles described herein. Exemplary processing agents/aids can include solid or liquid materials. The processing agents/aids may provide various extrusion benefits, and may include silicone based oil, wax and free flowing fluoropolymer. In other embodiments, the processing agents/aids may include compatibilizers/coupling agents, e.g., organosilicon compounds such as organo-silanes/siloxanes that are typically used in processing of polymer composites for improving mechanical and thermal properties. Such compatibilizers/coupling agents can be used to surface modify the glass and can include (3-acryloxy-propyl) trimethoxysilane; N-(2-aminoethyl)-3-aminopropyltrimethoxysilane; 3-aminopropyltri-ethoxysilane; 3-aminopropyltrimethoxysilane; (3-glycidoxypropyl) trimethoxysilane; 3-mercapto-propyltrimethoxysilane; 3-methacryloxypropyltrimethoxysilane; and vinyltrimethoxysilane.

In some embodiments, the materials described herein may include fillers including pigments, that are typically metal based inorganics can also be added for color and other purposes, e.g., aluminum pigments, copper pigments, cobalt pigments, manganese pigments, iron pigments, titanium pigments, tin pigments, clay earth pigments (naturally formed iron oxides), carbon pigments, antimony pigments, barium pigments, and zinc pigments.

After combining the copper-containing glass described herein with a carrier, as described herein, the combination or resulting material may be formed into a desired article or be applied to a surface. Where the material includes paint, the paint may be applied to a surface as a layer. Examples of such articles that may be formed using the material described herein include housings for electronic devices (e.g., mobile phones, smart phones, tablets, video players, information terminal devices, laptop computer, etc.), architectural structures (e.g., countertops or walls), appliances (e.g., cooktops, refrigerator and dishwasher doors, etc.), information displays (e.g., whiteboards), and automotive components (e.g., dashboard panels, windshields, window components, etc.).

The materials described herein may include pigments to impart color. Accordingly, the coatings or layers made from such materials may exhibit a wide variety of colors, depending on the carrier color, mixture of carriers and amount of particle loading. Moreover, the materials and/or coatings described herein showed no adverse effect to paint adhesion as measured by ASTM D4541. In some instances, the adhesion of the material or coating to an underlying substrate was greater than the cohesive strength of the substrate. In other words, in testing, the adhesion between the coating or coating and the substrate was so strong that the underlying substrate failed before the coating was separated from the surface of the substrate. For example, where the substrate includes wood, the adhesion between the coating or layer and the substrate may be about 300 psi or greater, 400 psi or greater, 500 psi or greater, 600 psi or greater and all ranges-sub-ranges therebetween, as measured by ASTM D4541. In some instances, the material, when applied to a substrate as a coating or layer, exhibits an anti-sag index value of about 3 or greater, about 5 or greater, 7 or greater, 8 or greater, 9 or greater, 10 or greater, 11 or greater, 12 or greater, 13 or greater, 14 or greater or even 15 or greater, as measured by ASTM D4400.

The material and/or coating may exhibit sufficient durability for use in household and commercial applications. Specifically, the material, when applied to a substrate as a coating or layer, exhibits a scrub resistance as measured by ASTM D4213 of about 4 or greater, 5 or greater, 6 or greater, 7 or greater and all ranges and sub-ranges therebetween.

In one or more embodiments, the material and/or coating may be resistant to moisture. For example, after exposure of the material and/or coating to an environment of up to about 95% relative humidity for 24 hours, the material and/or coating exhibited no change in antimicrobial activity.

One or more embodiments of the material may include an copper-containing glass and a carrier with a loading level of the copper-containing glass such that the material exhibits resistance or preservation against the presence or growth of foulants. Foulants include fungi, bacteria, viruses and combinations thereof. In some instances, the presence or growth of foulants in materials, such as paints, varnishes and the like, can cause color changes to the material, can degrade the integrity of the material and negatively affect various properties of the material. By including a minimum loading of copper-containing glass, (e.g., about 5 wt % or less, about 4 wt % or less, about 3 wt % or less, about 2 wt % or less, or about 1 wt % or less) to the carrier, the foulants can be eliminated or reduced. In some instances, the carrier formulation need not include certain components, when fouling is eliminated or reduced. Thus, the carrier formulations used in one or more embodiments of the materials described herein may have more flexibility and variations than previously possible, when in known materials that do not include the copper-containing glass.

EXAMPLES

Various embodiments will be further clarified by the following examples.

Comparative Example 1

The L* and C* values of Comparative Examples 1A-1E were evaluated. Comparative Example 1A included a white colored control paint only, which did not exhibit any antimicrobial activity. Comparative Examples 1B-1D included the same control paint as Comparative Example 1A but included copper-containing glass particles (having a composition of 45 mol % $SiO_2$, 35 mol % CuO, 7.5 mol % $K_2O$, 7.5 mol % $B_2O_3$ and 5 mol % $P_2O_5$) and the commonly used whitening agents of carbon black, zinc oxide, $TiO_2$, as shown in Table 1. Comparative Example 1E included the same control paint as Comparative Example 1A and the same copper-containing glass particles but no whitening agent, as shown in Table 1.

TABLE 1

Comparative Examples 1A-1E.

| Example | Paint | Antimicrobial additive | Whitening additive |
|---|---|---|---|
| Comparative Example 1A | white colored paint | None | None |
| Comparative Example 1B | white colored paint | Copper-containing glass particles, 100 g/gallon | Carbon black, 0.9 g/gallon |
| Comparative Example 1C | white colored paint | Copper-containing glass particles, 100 g/gallon | Zinc oxide, 4.5 g/gallon |
| Comparative Example 1D | white colored paint | Copper-containing glass particles, 100 g/gallon | $TiO_2$, 1 wt % |
| Comparative Example 1E | white colored paint | Copper-containing glass particles, 100 g/gallon | None |

Figure 1:
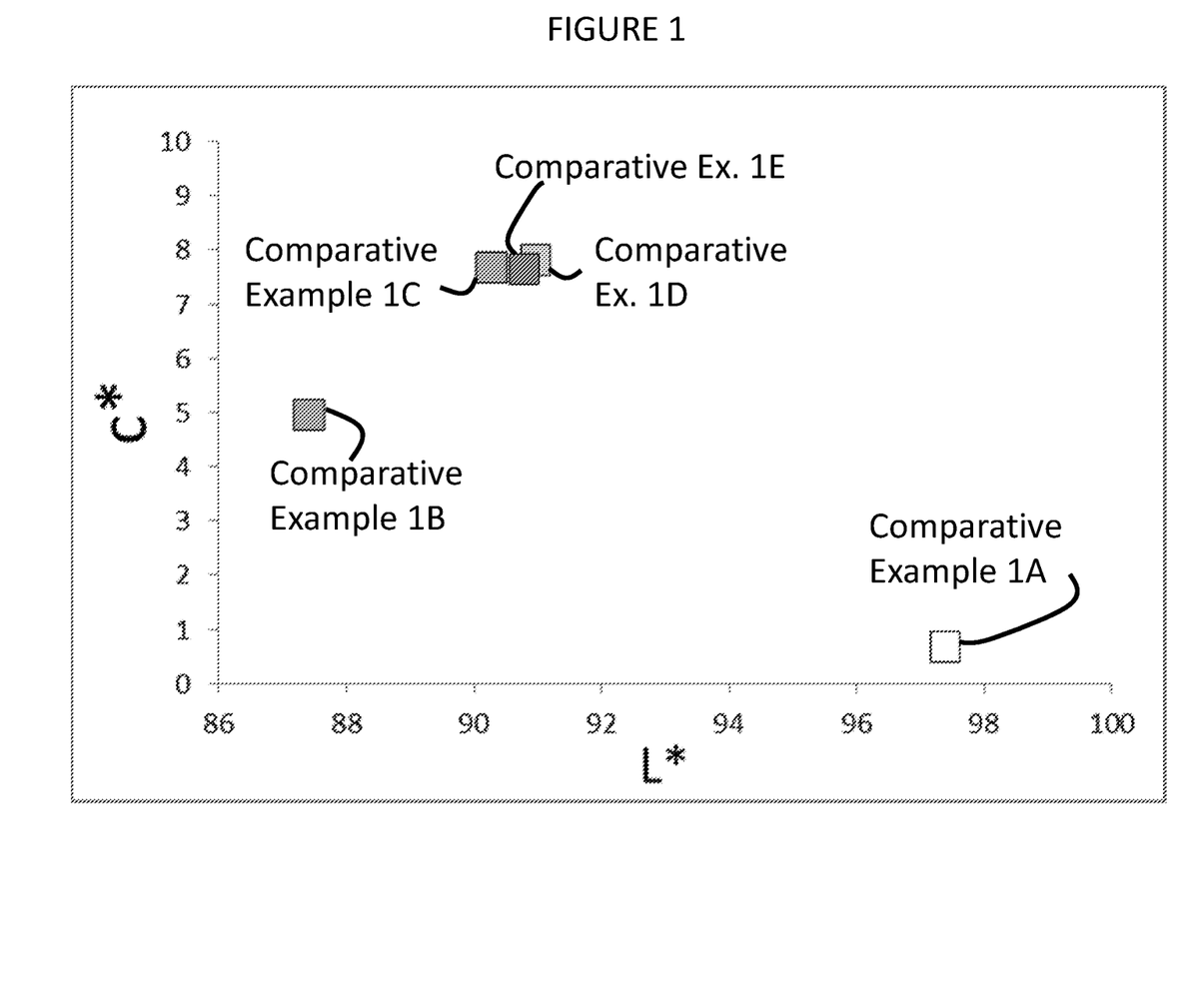
FIG. 1 is a graph showing the C* and L* values of Example 1.

The paint formulations of Comparative Examples 1A-1E were mixed and, 12 hours after mixing, each of the paints was applied to a plastic substrate and dried for 24 hours. The L* and C* values were measured immediately thereafter and plotted in FIG. 1. As shown in FIG. 1, Comparative Examples 1C and 1D did not impact the C* and L* values, when compared to the C* and L* values of Comparative Example 1A. Comparative Example 1B reduced reduce the C* value but also reduced the L* value (i.e., changing the color from light orange to darker grey color). To study the effects of longer term storage, the mixed paints were stored in a can for week and applied to the same plastic substrates for color measurement. After storage, the Comparative Example 1D exhibited a significantly reduced C* value.

Example 2

Example 2A and Example 2B and Comparative Examples 2C and 2D, each included two different white control paints from those used in Example 1, but used the same copper-containing glass particles and concentration of such particles as Comparative Example 1E. Examples 2A and 2B included sodium thiocyanate, and Comparative Examples 2C and 2D did not include sodium thiocyanate, as shown in Table 2. Control paint A was a commercially available, semi-glass white base paint supplied by Behr Process Corporation, and control paint B was a flat white base paint.

TABLE 2

Examples 2A-2B and Comparative Examples 2C-2D.

| Example | Paint | Antimicrobial additive | Whitening additive |
|---|---|---|---|
| Example 2A | Control A | Copper-containing glass particles, 100 g/gallon | Sodium thiocyanate, 10 g/gallon |
| Example 2B | Control B | Copper-containing glass particles, 100 g/gallon | Sodium thiocyanate, 10 g/gallon |
| Comparative Example 2C | Control A | Copper-containing glass particles, 100 g/gallon | None |
| Comparative Example 2D | Control B | Copper-containing glass particles, 100 g/gallon | None |

Figure 2:
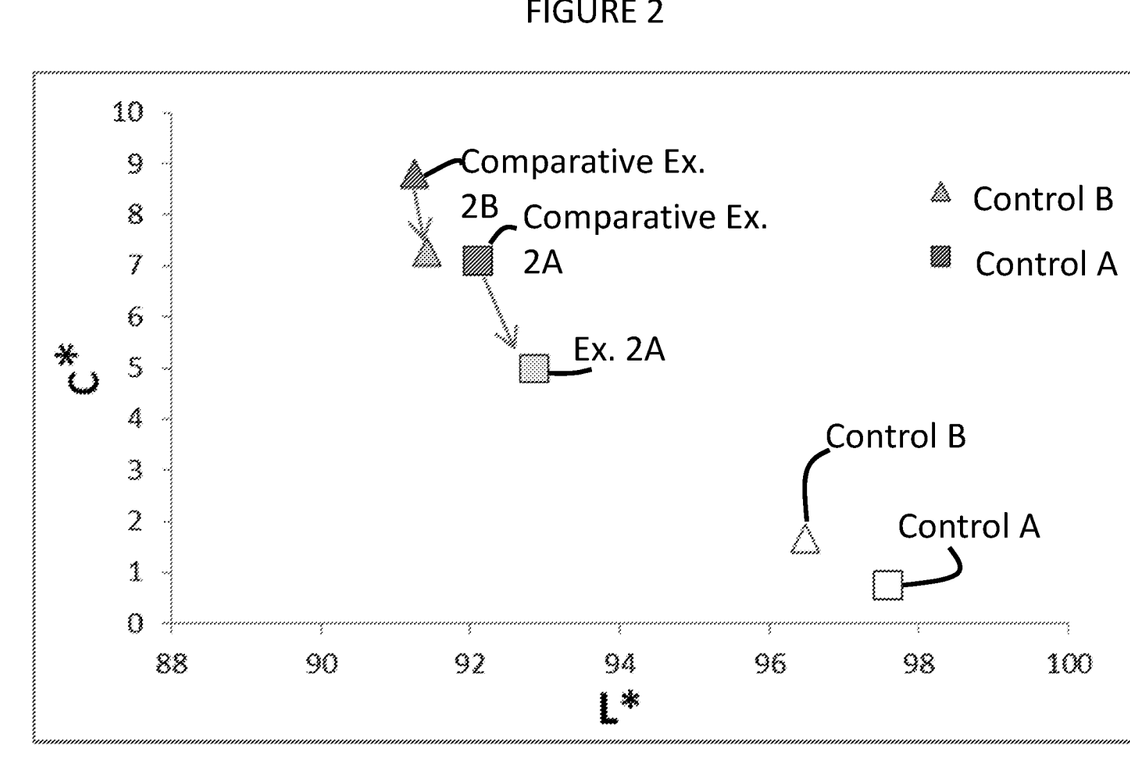
FIG. 2 is a graph showing the C* and L* values of Example 2.

The resulting paints were mixed and, 12 hours after mixing, each of the paints was applied to a plastic substrate and dried for 24 hours. The L* and C* values were measured thereafter and are plotted in FIG. 2. As shown in FIG. 2, the addition of sodium thiocyanate significantly reduced C* and increased L* values, with respect to Comparative Example 1E, in both Example 2A and 2B.

Figure 3:
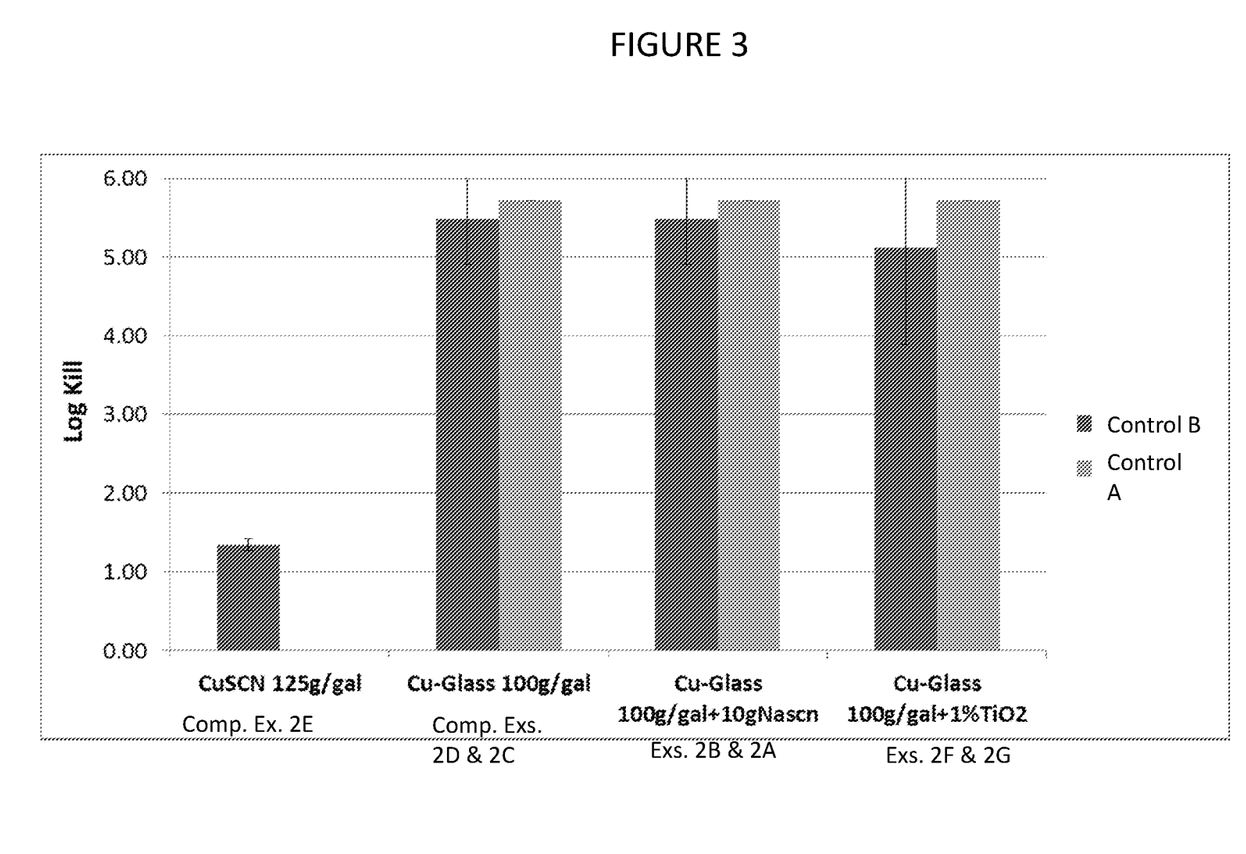
FIG. 3 is a graph showing the antimicrobial activity of Example 2.

Examples 2A-2B, Comparative Examples 2C-2E were then tested for antimicrobial efficacy under the EPA Test against *Staphylococcus aureus*. Comparative Example 2E included Control paint B and 125 g sodium thiocyanate per gallon of paint, but no copper-containing glass particles. As shown in FIG. 3, the addition of sodium thiocyanate did not adversely affect the antimicrobial activity of paint that included the copper-containing glass particles and the efficacy met the target of greater than 3 log reduction, necessary for a health benefit claim under the EPA Test. In contrast, sodium thiocyanate dispersed in control paint B alone, did not show antimicrobial activity under the EPA Test.

FIG. 3 also shows Examples 2F and 2G, as shown in Table 3, which exhibited substantially the same antimicrobial performance as each other and as Examples 2A-2B and Comparative Examples 2C-2D. As noted above, Examples 2F and 2G exhibited a whiter or more colorless appearance after painting. After being allowed to dry for 24 hours, the layer exhibited a substantially colorless or white appearance, as described herein.

TABLE 3

Examples 2F and 2G.

| Example | Paint | Antimicrobial additive | Whitening additive |
|---|---|---|---|
| Example 2F | Control B | Copper-containing glass particles, 100 g/gallon | Titanium dioxide, 1 wt % |
| Example 2G | Control A | Copper-containing glass particles, 100 g/gallon | Titanium dioxide, 1 wt % |

Example 3

Figure 4:
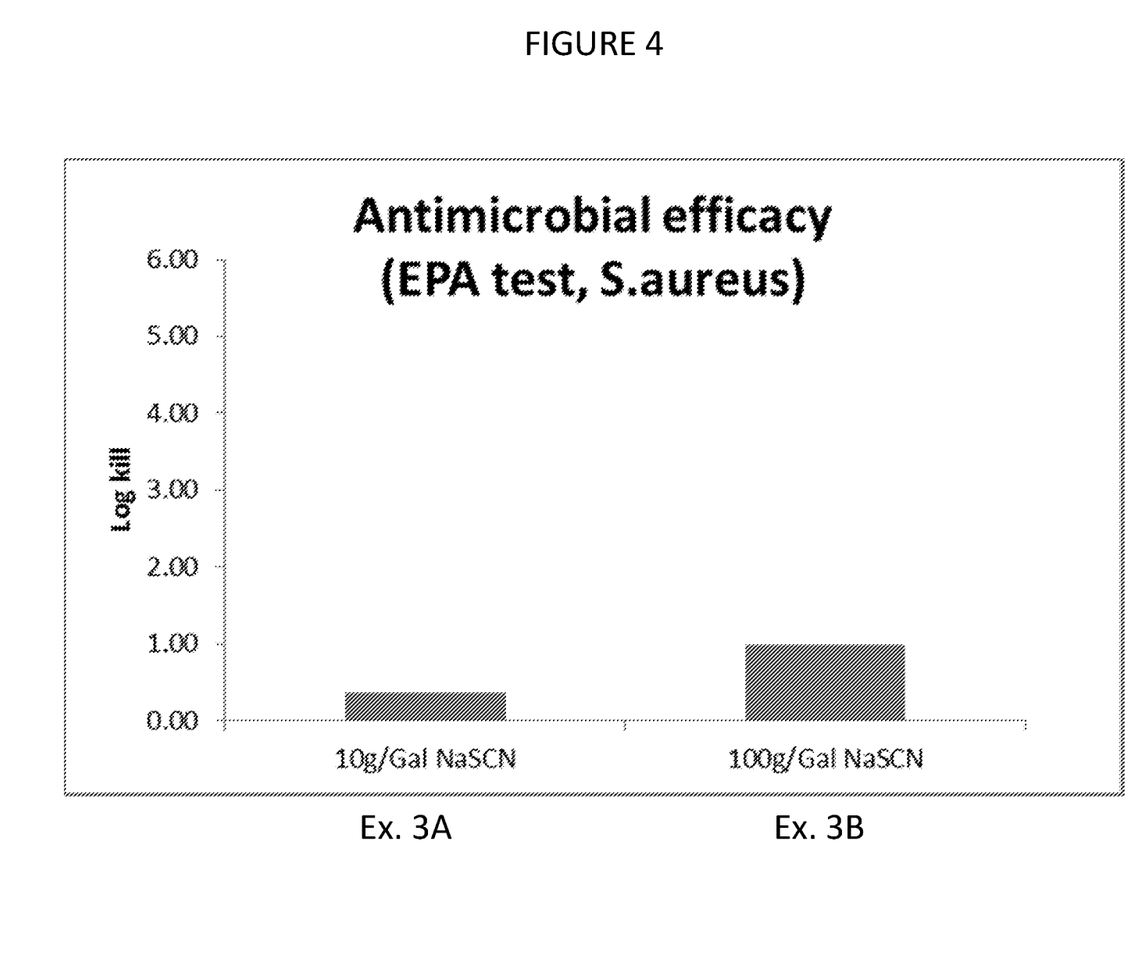
FIG. 4 is a graph showing the antimicrobial activity of Example 3.

Sodium thiocyanate is also a recognized antimicrobial agent and preservative, typically used in food and cosmetics. The antimicrobial activity of sodium thiocyanate in the paint alone (without the copper-containing particles) was evaluated under the EPA Test to rule out the possibility that antimicrobial activity of Examples including copper-containing particles and sodium thiocyanate was induce by the sodium thiocyanate itself. Comparative Examples 3A and 3B included the same white base paint as one another and different concentrations of sodium thiocyanate (Example 3A included 10 g per gallon, and Comparative Example 3B included 100 g per gallon). The resulting paints were applied on plastic substrates and cured at room temperature in air for 24 h prior to antimicrobial testing under the EPA Test against *Staphylococcus aureus*. FIG. 4 shows that addition of sodium thiocyanate to paint did not result in significant antimicrobial activity. Accordingly, the 10 g/gallon concentrations used in Example 2 did not contribute significantly to the observed antimicrobial activity.

It will be apparent to those skilled in the art that various modifications and variations can be made without departing from the spirit or scope of the invention.

What is claimed is:

1. A colorless material comprising
   a carrier;
   copper-containing particles; and
   sodium thiocyanate, wherein the material exhibits, in the CIE L*a*b* system, an L* value in the range from about 91 to about 100, and a C* value of less than about 7, wherein C* equals $\sqrt{(a*^2+b*^2)}$, and wherein the material exhibits a greater than 3 log reduction in a concentration of *Staphylococcus aureus*, under the EPA Test Method for Efficacy of Copper Alloy as a Sanitizer testing conditions.

2. The material of claim 1, wherein the copper-containing particles comprise a copper-containing glass.

3. The material of claim 1, wherein the copper-containing particles comprise cuprous oxide.

4. The material of claim 1, wherein the copper-containing particles are present in an amount of about 200 g/gallon of the carrier or less.

5. The material of claim 1, wherein the sodium thiocyanate is present in an amount of about 100 g/gallon or less.

6. The material of claim 1, wherein the carrier comprises a polymer, a monomer, a binder or a solvent.

7. The material of claim 1, wherein the carrier comprises paint.

8. The material of claim 2, wherein the copper-containing glass comprises a cuprite phase comprising a plurality of $Cu^{1+}$ ions, and comprising at least one of $B_2O_3$, $P_2O_5$ and $R_2O$, wherein R is at least one of K, Na, Li, Rb, and Cs.

9. The material of claim 8, further comprising a glass phase, wherein the glass phase comprises more than 40 mol % $SiO_2$.

10. The material of claim 8, wherein the cuprite phase is degradable and leaches in the presence of water.

11. A paint comprising:
   a plurality of cuprous ions,
   sodium thiocyanate,
   wherein the paint exhibits a 99% or greater reduction in a concentration of *Staphylococcus aureus*, under the EPA Test Method for Efficacy of Copper Alloy as a Sanitizer testing conditions, and
   wherein the paint exhibits, in the CIE L*a*b* system, an L* value in the range from about 90 to about 100, and a C* value of less than about 9, wherein C* equals $\sqrt{(a*^2+b*^2)}$.

12. The paint of claim 11, further comprising copper-containing particles, wherein the particle comprise either one or both of copper-containing glass and cuprous oxide, wherein the copper-containing particles are present in an amount of about 200 g/gallon or less.

* * * * *